United States Patent [19]

Kondo et al.

[11] Patent Number: 5,210,020

[45] Date of Patent: May 11, 1993

[54] IMMUNOASSAY UTILIZING ALGINATE TO ENHANCE SIGNAL TO NOISE RATIO

[75] Inventors: Koichi Kondo, Sohraku; Marvin A. Motsenbocker, Amagasaki, both of Japan

[73] Assignee: Takeda Chemical Industries, Ltd., Osaka, Japan

[21] Appl. No.: 651,261

[22] PCT Filed: Feb. 22, 1991

[86] PCT No.: PCT/JP91/00220

§ 371 Date: Apr. 8, 1991

§ 102(e) Date: Apr. 8, 1991

[87] PCT Pub. No.: WO91/13357

PCT Pub. Date: Sep. 5, 1991

[30] Foreign Application Priority Data

Feb. 28, 1990 [JP] Japan ................................. 2-050213

[51] Int. Cl.$^5$ ............................................. G01N 33/53
[52] U.S. Cl. .................................... 435/7.94; 435/962; 436/518; 436/531; 436/826
[58] Field of Search ...................... 435/7.1, 7.92, 7.94, 435/962; 436/518, 825, 826, 531

[56] References Cited

U.S. PATENT DOCUMENTS 4,997,836  5/1991  Sugihara et al. ................ 544/359 X
5,077,198 12/1991  Shih et al. ............................ 435/7.9

FOREIGN PATENT DOCUMENTS 0056254  1/1982  European Pat. Off. .
0140489  8/1984  European Pat. Off. .
0133976  3/1985  European Pat. Off. .
0331327  2/1989  European Pat. Off. .
5925184 12/1978  Japan .
 634147  8/1979  Japan .

OTHER PUBLICATIONS

Yanagisawa et al., *Nature*, vol. 332, pp. 411–415, (1988).
Sigma Chemical Company, 1988 Price List, p. 317.
Hashida, et al., Clinica Chimica Acta, 135:263–273 (1983).
Kato, et al., FEBS Letters, 99(1):172–174 (1979).
Johnson, et al., Gene Anal. Tech., 1:3–8 (1984).
Chemical Abstracts, vol. 99, No. 9, Aug. 29, 1983, (Columbus, Ohio, US), J. F. Kennedy et al., p. 456, abstract 68597z, & Eur. J. Biochem. 1983, 138 (3), 697–705.

*Primary Examiner*—Esther L. Kepplinger
*Assistant Examiner*—Susan C. Wolski
*Attorney, Agent, or Firm*—David G. Conlin; Linda M. Buckley

[57] ABSTRACT

Inclusion of alginate in enzyme-conjugate incubation solutions is used to improve performance of immunoassays. The total binding of antibody-signal producing species conjugate is enhanced and the specific binding is enhanced more than the non-specific binding. This allows a lower detection limit to be achieved in these assays.

6 Claims, 2 Drawing Sheets ical field of
IMMUNOASSAY UTILIZING ALGINATE TO ENHANCE SIGNAL TO NOISE RATIO

DESCRIPTION

1. Technical Field

The present invention relates generally to the field of quantitation of water borne analytes by immunoassays and, specifically, with assay conditions that enhance the binding reactions that occur in these assays.

2. Background Art

One of the most sensitive versions of immunoassays is the sandwich technique. This technique includes two binding reactions. In one, a sample analyte molecule to be quantitated is bound to an antibody immobilized to a solid phase support (first binding), and the excess unbound sample analyte molecule is removed by washing. In the second, an excess amount of a labeled antibody is added thereto to bind it to the sample analyte molecule on the support (second binding). Thus, the analyte molecule is sandwiched between the immobilized antibody and the labeled antibody and the excess unbound labeled antibody is removed by washing. Finally, a signal is developed from a label substance (e.g., enzymes, radioactive isotopes, etc.) of the labeled antibody by suitable means. The amount of the analyte molecule is determined by measuring the amount of the signal. This is the normally employed general sandwich technique. In addition to this, there is another technique wherein a sample analyte molecule to be quantitated is firstly reacted with a labeled antibody and then they are added to an immobilized antibody to form a sandwich (reverse sandwich technique), or an immobilized antibody, a sample analyte molecule to be quantitated and labeled antibody are simultaneously admixed to react them (one step sandwich technique).

The above two binding reactions of a sandwich technique are of paramount importance. Specific binding among the immobilized enzyme, the analyte molecule and the labeled antibody that takes place during the first and second binding reactions results from the specific affinity among them (e.g., between the antigen and the antibody, etc.). On the other hand, non specific binding is defined as accidental binding of the labeled antibody to the solid phase directly. This type of binding causes a background signal in the assay that is not proportional to the analyte concentration. These specific binding and non-specific binding reactions significantly influence sensitivity and performance of these assays. Thus, one aim of the art is to minimize non-specific binding of the labeled antibody to the support and maximize specific binding between the labeled antibody and analyte bound to the support.

A technique found to be useful for this aim has been to include particular substances which have the property of increasing the specific binding or decreasing the non-specific binding in an incubation solution (reaction mixture) containing (1) the analyte molecule bound to the immobilized antibody and the labeled antibody, (2) the immobilized antibody and the analyte molecule bound to the label substance, or (3) the immobilized antibody, the label substance and the analyte molecule. For example, it was shown that use of high salt concentration in an ELISA (Enzyme Linked Immunosorbent Assay) incubation solution frequently improves the binding reactions [Hashida et al., Clin. Chim. Acta, 135, 263–273 (1983)]. Others have found that inclusion of gelatin in an incubation solution is helpful to decrease non-specific binding and thereby improve sensitivity of ELISAs [Kato et al., Febs. Lett. 99, 172–174 (1979)]. Proteolytically degraded gelatin was also found to be helpful in this regard. Milk protein (casein) is another additive that was found to improve assay performance by decreasing non-specific binding [Johnson et al., Gene. Anal. Techn., 1, 3–8 (1984)]. Although these substances alleviate the problem, they do not work in every system and also much more needs to be done to lower the non-specific binding of labeled antibody to the solid phase support. Additionally, many of these substances decrease both specific and non-specific binding. This creates a new problem by lowering detection sensitivity. For example, addition of extra protein to an incubation solution containing the labeled antibody may decrease non-specific binding, but this is done at the expense of lowering total binding. By lowering total binding, the total signal is reduced and readout detection sensitivity is adversely affected. The problem of non-specific binding limitation to assay sensitivity was studied from a theoretical basis by Ekins [Ekins et al., J. Biolum. Chemilum. 4, 59–78 (1989)] who concluded that although there have been some advances in this aspect of immunoassays, much more needs to be done.

In addition to these binding reactions, it is also of importance in immunoassays to develop a signal and to detect it. For example, in order to detect 1 attomole of an analyte by ELISA, one needs to have a significantly high proportion of analyte molecules participate in sandwich formation reactions and one must be able to detect less than one attomole in the readout reaction. Thus, any method which either increases the proportion of analyte molecules that become bound in the assay or which increases the overall signal produced in the signal readout step is of importance in immunoassays.

OBJECTS OF THE INVENTION

The general object of the present invention is to increase the overall signal produced in immunoassays by improving binding reaction efficiency between the analyte molecule and the labeled antibody in the case of (1) binding of the analyte molecule to the immobilized antibody and then binding the labeled antibody thereto; (2) binding of the labeled antibody to the analyte molecule and then binding the immobilized antibody thereto; or (3) a simultaneous reaction of the immobilized antibody, the analyte molecule and the labeled antibody. There are some objects regarding increase in the overall signal at the readout step of a typical signal.

One object is to shorten the time required for measuring the signal. Presently, this signal development time can be longer than one hour for the most sensitive ELISAs. Many enzymes are not perfectly stable in buffer solutions for long periods of time during the measurement. In the present invention, an advantage is that enzymes that have poor stability can be more easily accommodated in these assays by shortening the time required for the measurement.

A second object is to decrease the reaction volume needed to perform a measurement. This is especially important where the fluid sample to be analyzed by the ELISA is scarce or difficult to get in large quantity, such as for example, blood from a newborn.

Another object of the present invention is to allow higher concentrations of other additives to be used in the incubation solution containing the labeled antibody. For example, when bovine serum albumin, sodium chloride or block ace which increases the specific binding/non-specific binding signal readout ratio (S/N) is added in a high concentration, these substances lower the total signal and in extreme cases there is not enough signal produced in the readout step for the measurement to be meaningful. The present invention solves this problem.

Yet another object of the present invention is to improve (decrease) the coefficient of variation in the measurement. For enzyme readout reactions that generate very small changes in signal, it can be determined that improving the overall signal has a direct advantage in the assay precision [Klee and Post, Clin. Chem., 35, 7, 1362–1366 (1989)].

An object of the present invention is to improve the S/N ratio obtained from immunoassay measurements.

These objects as well as other objects and advantages of the present invention will be apparent to those skilled in the art from the following description with reference to the attached drawings.

SUMMARY OF THE INVENTION

Figure 1:
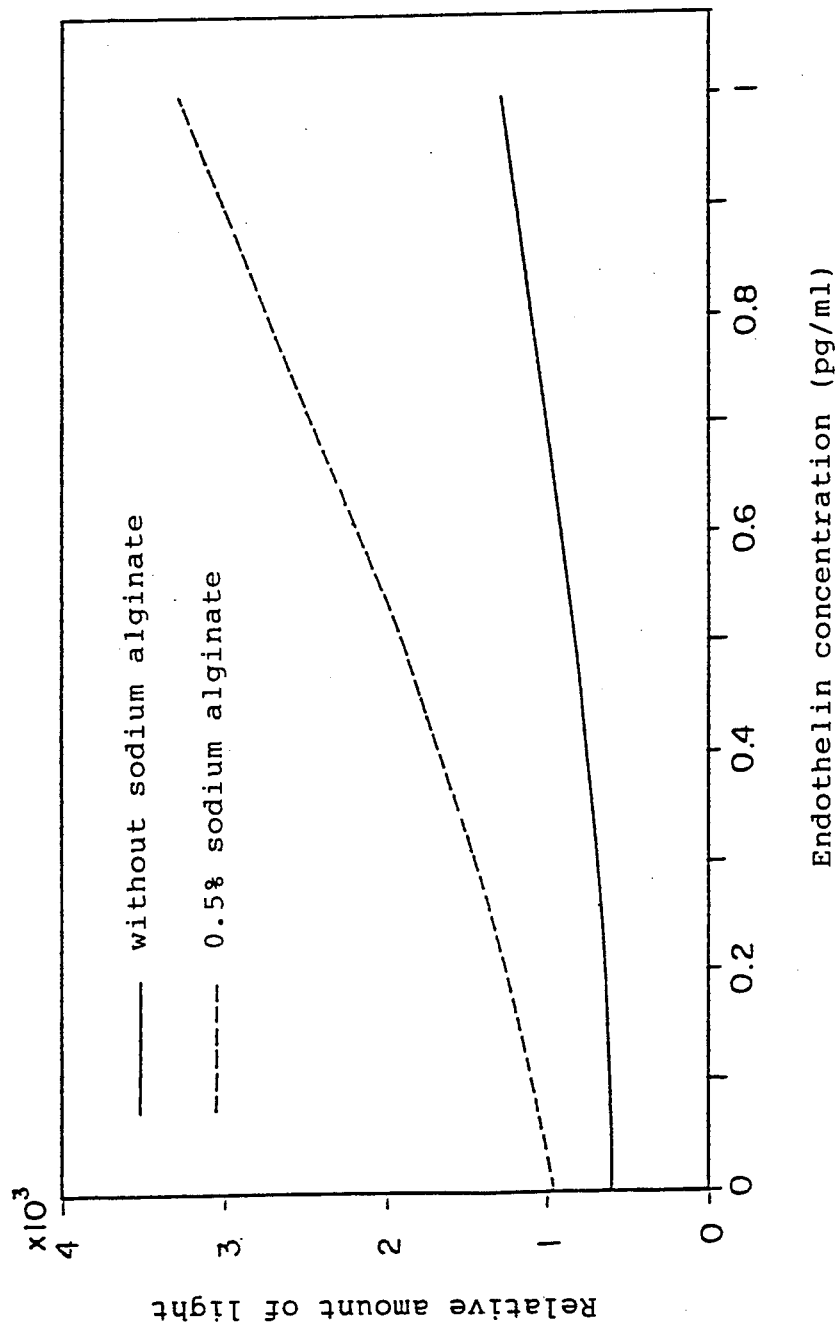
FIG. 1 is a graph showing the increase in the relative amount of light by addition of sodium alginate in the immunoassay of endothelin of Example 1 hereinafter.

The present inventors have intensively studied additives which can attain to the above objects in immunoassays using the sandwich technique. As a result, it has been found that the proportion of the labeled antibody bound in the second binding reaction can be increased by addition of an alginate or its partial hydrolyzate to a buffer solution containing the labeled antibody to increase the overall signal.

Namely, according to the present invention, there is provided an improved sandwich-type immunoassay method, wherein the improvement comprises subjecting the labeled antibody to a binding reaction to the analyte in the presence of an alginate, a partially hydrolyzed alginate or mixture thereof.

In the method of the present invention, the labeled antibody may be an antibody-enzyme conjugate and the conjugate may be incubated together with immobilized analyte.

DISCLOSURE OF THE INVENTION

The alginate used in the present invention is preferably sodium alginate (straight chain polyuronic acid composed primarily of anhydro-b-D-mannuronic acid residues with 1–4 linkage). Not all commercially available sodium alginates are equal in causing the improvement to the immunoassay system. In general, the commercial batches of alginate that are best are fine powders having no evidence of yellow impurities. Algins that appear yellow or off-white to the naked eye are generally less suitable for the present invention. The algin is also preferably purified by organic solvent precipitation from water solution and most preferably with acetone although exposure of aqueous algin solutions to charcoal followed by removal of charcoal also has value in improving the quality of the alginate. The molecular weight of the alginate is not especially critical.

The algin may be partially hydrolyzed. It is preferred to use as high a concentration of alginate as possible because the stimulation of performance caused by the alginate is higher at higher alginate concentrations. At very high alginate concentration, however, the viscosity of the binding reaction solution is so high that the removal of solvent is difficult in the subsequent washing step. Therefore, the algin may be partially hydrolyzed to decrease its viscosity while retaining or increasing its beneficial properties. Such partially hydrolyzed algin was found to greatly improve immunoassay performance by allowing the use of higher concentrations of alginate while keeping the viscosity of the algin solution at a low level. Acid hydrolysis of algin followed by neutralization with a base and purification is preferred. The use of the acid HCl and the base sodium hydroxide followed by purification via acetone precipitation is especially preferred. It is preferred to partially hydrolyze algin in the concentration range of 0.1% to 5% (w/v). Solutions of 2% (w/v at 25° C.) alginate that exhibit viscosities in the range of 1 to 10,000 cps are especially suitable.

The alginate or partial hydrolyzate of algin (hereinafter sometimes merely referred to as algin) is used in the binding reaction at a concentration of 0.1% to 10%.

The pH of the algin solution used is also not critical and may vary between pH 5 and pH 10. A pH between 6 and 8 is preferred due to the pH requirements of the labeled antibody employed in the binding reaction that is enhanced by algin.

The time duration of algin exposure in the binding reaction is also not critical. A time period of between 0.1 and 48 hours is acceptable and between 0.2 and 12 hours is most preferable due to the kinetic behavior of the labeled antibody commonly used.

Temperature of the binding reaction in which algin is used is likewise not limited by the algin but instead by requirements of the agent to be used. A temperature of 4 to 35° C. is preferred due to the needs of the immobilized antibody.

The analyte molecules to be measured by the immunoassays of the present invention are those utilized in clinical tests. Examples include proteins, peptides and hormones contained in body fluids such as human immunoglobulins, human albumin, human fibrinogen (fibrin and its degradation products), α-fetoprotein, C-reactive protein, $\beta_2$-microglobulin, myoglobin, carcinoembryonic antigen, hepatitis virus, human chorionic gonadotropin, human placental lactogen, insulin and the like as well as drugs and antibodies of these molecules.

The antibodies used for the immobilized antibody and the labeled antibody in the present invention are those against the above analyte molecules. In many cases, the antigen recognition sites of these antibodies are different from each other. However, both antibodies may have a common recognition site.

The label substance bound to the antibody of the labeled antibody may be a radioactive isotope used in a conventional RIA (radioimmunoassay), enzyme used in a conventional ELISA, co-enzyme, enzyme modulator or the like. Preferably, peroxidase is used. The source of peroxidase is not limited and there can be used peroxidase from vegetable such as horseradish, yeasts, bacteria and the like.

Examples of the support used for immobilizing the antibody include agarose gel (e.g., Sepharose 4B and Sepharose 6B manufactured by Pharmacia Fine Chemical AB, Sweden), dextran gel (e.g., Sephadex G-75, Sephadex G-100 and Sephadex G-200 manufactured by Pharmacia Fine Chemical AB, Sweden), polyacrylamide gel (e.g., Bio Gel P-30, Bio Gel P-60 and Biogel P-100 manufactured by Bio Rad Laboratories Inc., U.S.A.), cellulose particles [e.g., Avicel manufactured by Asahi Chemical Co., Ltd., Japan, and ion exchange cellulose (e.g., diethylaminoethyl cellulose, carboxymethyl-cellulose)], physical adsorbents [e.g., glass (e.g., glass beads, glass rods, aminoalkyl glass beads, aminoalkyl glass rods), silica flakes, styrene resin (e.g., polystyrene beads, polystyrene particles), and microtiter plates for immunoassays (e.g., plate manufactured by Dynatech Laboratories, Inc., U.S.A.)], ion exchange resin [e.g., weak acidic cation exchange resin (e.g., Amberlite IRC-50 manufactured by Rohm & Haas Co., U.S.A. and Zeo-Karb 226 manufactured by Permutit AG, Germany) and weak basic anion exchange resin (e.g., Amberlite IR-4B manufactured by Rohm & Haas Co., U.S.A., and Dowex 3 manufactured by Dow Chemical Co., U.S.A.)] and the like.

The immobilization of the antibody on the support can be conducted by a conventional method. For example, bromcyan method and glutaric aldehyde method described in "Taisha (Metabolism)", Vol. 8 (1971), page 698 can be employed. As a more simple method, the antibody can be immobilized on the support by physical adsorption.

For example, the following kit can be used for conducting the improved immunoassay of the present invention:

(1) The antibody immobilized on the support;
(2) The labeled antibody dissolved in a buffer solution containing the algin;
(3) The standard sample of the analyte molecule;
(4) A buffer solution used for dilution of the the above standard sample (3) and a sample to be tested (The buffer may be any one which can be used for dilution of these agents and sample. Examples thereof include phosphate buffer and glycine buffer of pH 6 to 9.);
(5) A buffer solution used for washing the support after incubation (The buffer may be any one which can be used for washing the support. Examples thereof include phosphate buffer and glycine buffer.); and
(6) In the case of using an enzyme as the label substance, the agents necessary for measuring the enzyme.

When peroxidase is used as the enzyme, examples of the agents for measuring it include p-hydroxyphenylacetic acid as the substrate and hydrogen peroxide in the case of fluorescence method, or o-phenylenediamie and hydrogen peroxide in the case of colorimetry; a buffer solution for dissolving the substrate of the enzyme (preferably citrate buffer), and a solution for terminating the enzymatic reaction. Further, in the case of a chemiluminescence method, an enhancer of chemiluminescence and the like are included. Furthermore, in the case of using a chemilumigenic substance as the label substance, agents for measuring the substance are included. Examples thereof are an oxidizing agent (preferably, hydrogen peroxide) in the case of luminol, a catalyst (microperoxidase, hypochlorite, etc.) and a buffer solution for dissolving the oxidizing agent and catalyst (preferably, sodium hydroxide solution or carbonate buffer solution).

Preferably, the above kit is used as follows:

A solution of the standard sample or a sample to be tested (about 10 to 200 μl) is diluted with the agent (4), the diluted solution is reacted with the agent (1) at about 0° to 40° C. for about 10 minutes to 2 days and the reaction mixture is washed with the agent (5). Then, after addition of the agent (2) (about 10 to 300 μl), the mixture is reacted at about 0° to 40° C. After the reaction for about 10 minutes to 2 days, the mixture is washed with the agent (5) and the the activity of the label substance bound to the support is measured. When the label substance is a radioisotope, it is measured with a well counter or a liquid scintillation counter according to a known method. When the label substance is an enzyme, its enzymatic activity is measured according to a known method (e.g., the methods described in Ishikawa et al., "Kosomeneki Sokutei-ho (Enzyme Immunoassays)", published by Igaku Shoin, pp. 67–81). Even if the label substance is a fluorescent substance or a luminescent substance, it can be measured according to a known method.

The algin can be admixed with the labeled antibody as in the agent (2) in advance, or the algin can be separately prepared.

In the present invention, a signal can be detected by a method commonly employed in RIAs and ELISAs. Particularly, ELISA utilizing a chemiluminescent reaction is preferred.

When ELISA was conducted according to the same manner as described hereinabove except that mannose, sucrose, ethanol, polyvinyl pyrrolidone, polyethylene glycol, SDS (sodium dodecyl sulfate), histone or thyroglobulin was added to a buffer containing the labeled antibody instead of the algin, any result comparable to that obtained by the method of the present invention could not be obtained.

The following Examples further illustrate the present invention in detail but are not to be construed to limit the scope thereof. In the following Examples, all parts and percents are by weight unless indicated otherwise except for mixtures of liquids which are by volume. The abbreviation BSA is bovine serum albumin (Code 250010 Crystallized, obtained from Seikagaku Kogyo Co. Tokyo, Japan).

All measurements were made on an automated microtiter plate chemiluminometer (Model ML1000, Dynatech Laboratories Inc. Chantilly, Va., U.S.A.) adjusted for high voltage setting and 0.25 second readings. All enzyme readout reactions were comprised of 2 mM luminol (recrystallized from 5% NaOH), 0.02 mM disodium ethylene diamine tetraacetate (hereinafter abbreviated as EDTA), 0.02 mM 4-(4-hydroxyphenyl)-thiazole and 0.25% ethanol in 0.1 M tris-HCl buffer (pH 8.7).

Endothelin [the polypeptide of 21 amino acid residues derived from endothelial cells, Yanagisawa et al., Nature, 332, pp. 411–415 (1988)] was used as the analyte molecule.

EXAMPLE 1

Immunoassay of Endothelin Enhanced by 0.5% Algin

This embodiment shows that addition of algin to the antibody-enzyme conjugate incubation solution increases the overall assay signal and improves the S/N.

White plastic microtiter plate wells (DYNATECH MicroFLUOR, Dynatech Laboratories, Inc. Chantilly, Va., U.S.A.) were incubated at room temperature for 3 hours with 0.1 ml of 50 μg/ml of monoclonal anti-endothelin antibody in 0.1M carbonate buffer (pH 9.5). The antibody preparation is described by Suzuki et al, J. Immun. Methods, 118, 245-250 (1989). The wells were rinsed thrice with 50 mM phosphate buffer (pH 7.0) (hereinafter abbreviated as PBS) and then 0.3 ml of 25% BLOCK ACE an additive for blocking non-specific binding (Cat. No. UK-B25 Snow Brand Products, Sapporo, Japan) in PBS was added per well. The plate was stored at 6° C. until use.

Endothelin (1-21, Peptide Institute Inc., Osaka, Japan) was diluted into 0.1% BSA with a final 100 fold dilution into endothelin incubation buffer (10% BLOCK ACE, 0.4M NaCl, 1 mM EDTA, 20 mM sodium phosphate pH 7.0). Then 0.1 ml portions of endothelin (0, 0.2 pg/ml, 0.5 pg/ml, and 1 pg/ml in replicates of three) in endothelin incubation buffer were added to separate wells of the microtiter plate and incubated for 16 hours. The wells were washed 3 times with PBS. One hundred microliters of conjugate incubation buffer (10% BLOCK ACE, 0.5% BSA, 0.4M NaCl, 1 mM disodium ethylene diamine tetraacetic acid, 20 mM sodium phosphate pH 7.0) that contained a 1:200 fold dilution of polyclonal anti-endothelin antibody horseradish peroxidase enzyme conjugate (Suzuki et al, J. Immun. Methods, 118, 245-250 (1989)) plus either 0% or 0.5% algin (Alginic Acid, Sodium Salt Cat. 196-01095, Wako Pure Chemicals, Tokyo, Japan) were slowly added to each well. The plate was incubated for 24 hours. The plate was washed 5 times with PBS and the horseradish peroxidase was quantified by an enhanced chemiluminescence reaction. Namely, emission was initiated by addition of 2 mM luminol, 500 μM hydrogen peroxide, 20 μM 4-(4-hydroxyphenyl)-thiazole as a sensitizer, 0.02 mM EDTA and 0.1M Tris buffer (pH 8.7) containing 0.25% ethanol and chemiluminescence measured for 0.25 second by a microplate chemiluminescence automatic measuring device (Model HL 1000 manufactured by Dynatech Laboratories, Inc., U.S.A.).

The samples that employed 0.5% algin in the conjugate incubation step produced three times as much light in the readout step than did samples that had no added algin.

FIG. 1 depicts endothelin standard curves obtained using 0% algin and 0.5% algin. The percent increase in signal produced at the signal development step as a result of algin addition to the preceding incubation step was of similar magnitude throughout the range studied. The ratio of signal produced at 1 pg/ml of endothelin divided by signal produced at 0 pg/ml (the S/N ratio) was 2.2 when 0% algin was used, and was 3.5 when 0.5% algin was used.

EXAMPLE 2

In this embodiment, commercially available algin was purified. The purified algin performed better than unpurified algin.

Algin was purchased from Sigma Chemical Company (Cat. 12345, medium viscosity). One half gram thereof was subjected to purification by the following procedure: A 2 percent solution was made in distilled water. This was diluted with acetone (475 ml). The precipitate was carefully washed in acetone, air dried, and rewashed. The procedure explained in example 1 was used to assay 0 and 1 pg/ml endothelin calibrators using 0.5% unpurified algin and also using 0.5% purified algin in the conjugate incubation medium. The average background signal produced by samples exposed to the unpurified algin was 772 and the average background signal produced by samples exposed to the purified algin was 221 (relative light units). Thus, the purification technique decreased the background binding by 71 percent. The average readout light signal was 1620 for 1 pg/ml of endothelin samples exposed to unpurified algin and was 818 for 1 pg/ml of endothelin samples exposed purified algin. Thus, for the immunoassay of endothelin at 1 pg/ml concentration, purification of algin increased the S/N ratio from 2.1 to 3.7.

EXAMPLE 3

In this embodiment, a19in of medium chain length was acid hydrolyzed to form algin of smaller chain length. The hydrolyzed algin was used in an immunoassay at the same viscosity as the unhydrolyzed algin and allowed greater sensitivity of the assay.

Algin was purchased from Wako Pure Chemical Company and used following acetone purification as described above. One and one quarter grams of the algin were subjected to the following hydrolysis procedure. Fifty ml of water were added to dissolve the algin and 200 ml of acetone added. Then, 200 ml of concentrated HCl were slowly added while stirring and the mixture incubated at room temperature for 1 hour or for 3 hours. The hydrolyzed algin was then neutralized to pH 7.5 by titration with 50% sodium hydroxide. Three liters of acetone were added to precipitate the algin. The precipitate was washed with 50% acetone and then air dried. The algin was then re-dissolved in 50 ml of hot water and re-precipitated by the addition of 1 liter of acetone. This was washed with acetone and air dried. The unhydrolyzed algin was used at a concentration of 0.5% in an endothelin immunoassay. It was found to be not possible to use higher concentrations than 0.5% because the solution viscosity was too high at higher concentrations. The one hour hydrolyzed algin was used at a concentration of 2.8%. The three hour hydrolyzed algin was used at a concentration of 3.6 percent. These concentrations of hydrolyzed algins were found to have the same solution viscosities as the 0.5% unhydrolyzed algin (20 cps).

Figure 2:
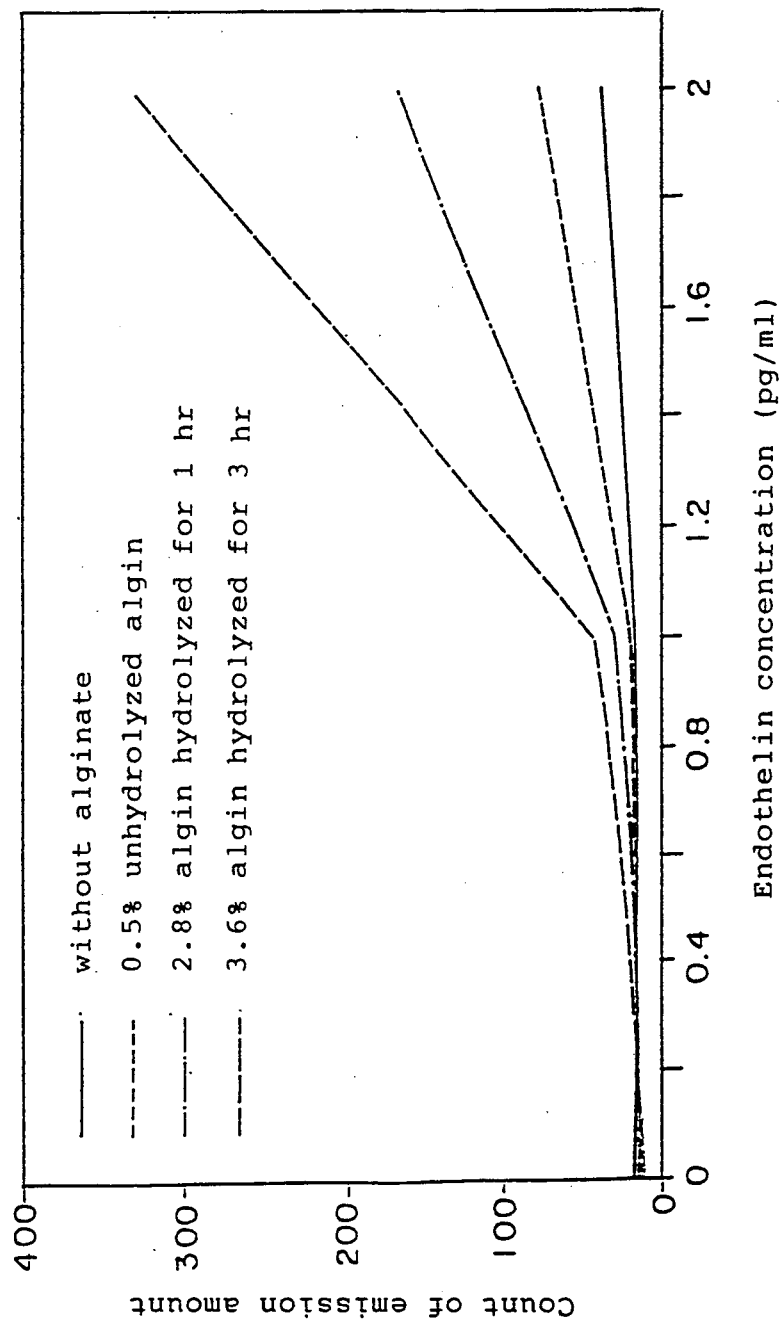
FIG. 2 is a graph showing the increase in the count of emission by addition of partially hydrolyzed algin in the immunoassay of endothelin of Example 3 hereinafter.

FIG. 2 depicts the results of an endothelin assay in which the three algin preparations were compared to each other and to a 0% algin control. This experiment was performed using the procedure of Example 1. The graph shows that although a 20 cps viscosity solution of algin improves the standard curve of endothelin measurement, use of 1 hour hydrolyzed algin and especially use of 3 hour hydrolyzed algin solutions at the same viscosity yielded further improvements in the total signal response. A statistical analysis was performed on this data (n=5) to determine the minimum endothelin concentrations that were detectable with at least 95% probability (the "detection limit"). The minimum detection limit was 0.058 pg for the no algin samples, 0.043 pg for the unhydrolyzed algin samples, 0.024 pg for the 1 hour hydrolyzed algin samples and 0.017 pg for the 3 hour hydrolyzed algin samples. Thus, in addition to increasing the total signal produced in the immunoassay, hydrolysis of algin allowed a lower detection limit to be achieved as well.

It will be understood that various modifications, changes, alterations and additions can be made in the method of the present invention, its steps and parameters. All such modifications, changes, alterations and additions are within the scope of the appended claims and form part of the present invention.

We claim:

1. In an immunoassay which comprises forming two specific binding reactions of (1) the first binding of a sample analyte molecule to an antibody immobilized to a solid phase support and (2) the second binding of a labeled antibody to the sample analyte molecule and determining the amount of the signal developed from the label, wherein the improvement resides in subjecting the labeled antibody to the second specific binding reaction to the analyte in the presence of an alginate, at a concentration of about 0.1% to 0.5% a partially hydrolyzed alginate, or a mixture thereof at a concentration of about 0.1% to 10%.

2. The method of claim 1, wherein the labeled antibody is an antibody-enzyme conjugate.

3. The method of claim 2, wherein the enzyme used is peroxidase.

4. The method of claim 1, wherein the analyte is endothelin.

5. The method of claim 1, wherein the alginate, the partially hydrolyzed alginate or the mixture thereof is purified.

6. The method of claim 5, wherein the purified alginate, the purified partially hydrolyzed alginate or the mixture thereof is obtained by organic solvent precipitation from an aqueous solution of an alginate, a partially hydrolyzed alginate or a mixture thereof.

* * * * *